(12) United States Patent
Fetissov et al.

(10) Patent No.: US 11,319,352 B2
(45) Date of Patent: May 3, 2022

(54) *BRASSICACEAE* PROTEIN EXTRACT AND USES THEREOF

(71) Applicants: TARGEDYS, Rouen (FR); INSERM (INSTITUT NATIONAL DE LA SANTÉ ET DE LA RECHERCHE MÉDICALE), Paris (FR); UNIVERSITÉ DE ROUEN, Mont-Saint-Aignan (FR)

(72) Inventors: Serguei Fetissov, Montigny (FR); Grégory Lambert, Châtenay-Malabry (FR); Romain Legrand, St Etienne du Rouvray (FR); Nicolas Lucas, Rouen (FR)

(73) Assignees: TARGEDYS, Rouen (FR); INSERM (INSTITUT NATIONAL DE LA SANTÉ ET DE LA RECHERCHE MÉDICALE), Paris (FR); UNIVERSITÉ DE ROUEN, Mont-Saint-Aignan (FR)

(*) Notice: Subject to any disclaimer, the term of this patent is extended or adjusted under 35 U.S.C. 154(b) by 193 days.

(21) Appl. No.: 16/500,494

(22) PCT Filed: Apr. 3, 2018

(86) PCT No.: PCT/EP2018/058453
§ 371 (c)(1),
(2) Date: Oct. 3, 2019

(87) PCT Pub. No.: WO2018/185082
PCT Pub. Date: Oct. 11, 2018

(65) Prior Publication Data
US 2021/0107952 A1 Apr. 15, 2021

(30) Foreign Application Priority Data
Apr. 3, 2017 (EP) .................................. 17305401

(51) Int. Cl.
*C07K 14/415* (2006.01)
*A23L 33/12* (2016.01)
*A23L 33/16* (2016.01)
*A61K 38/00* (2006.01)

(52) U.S. Cl.
CPC ............ *C07K 14/415* (2013.01); *A23L 33/12* (2016.08); *A23L 33/16* (2016.08); *A61K 38/00* (2013.01)

(58) Field of Classification Search
None
See application file for complete search history.

(56) References Cited

U.S. PATENT DOCUMENTS 8,557,963 B2 * 10/2013 Wanasundara ........ A23L 33/185
530/377

FOREIGN PATENT DOCUMENTS

| CN | 104286756 A | 1/2015 |
|---|---|---|
| WO | 2015/082633 A1 | 6/2015 |
| WO | 2015/082655 A1 | 6/2015 |
| WO | 2016/059455 A1 | 4/2016 |

OTHER PUBLICATIONS

Tennoune et al "Bacterial ClpB heat-shock protein, an antigen-mimetic of the anorexigenic peptide alpha-MSH, at the origin of eating disorders" Translation Psychiatry 4:e458. (Year: 2014).*
Breton et al. "Gut Commensal *E. coli* Proteins Activate Host Satiety Pathways following Nutrietn-Induced Bacterial Growth" Cell Metabolism 23:324-334. (Year: 2016).*
Kapusta-Duch et al. "The beneficial effects of *Brassica* vegetables on human health" Rocz Panstw Zakl High. 63:389-395 (abstract only) (Year: 2012).*
Wanasundara J "Proteins of *Brassicaceae* Oilseeds and their Potential as Plant Protein Source" Crit. Rev. Food Sci. Nutr. 51:635-677. (Year: 2011).*
Hashem et al "*Brassica oleracea* L.var. *italica*: A nutritional supplement for weight loss" Planta Med 75: PH28. (Year: 2009).*
Lee et al. "The *Arabidopsis* ClpB/Hsp100 family of proteins: chaperones for stress and chloroplast development" The Plant Journal 49:115-127. (Year: 2006).*
International Search Report dated Jun. 28, 2018 and Written Opinion in corresponding International application No. PCT/EP2018/058453; 13 pages.
Anonymous: DailyMed *Brassica napas* —brassica napus subsp. *napus* pellet11, Jul. 1, 2015, Retrieved from the Internet: URL:https://dailymed.nlm.nih.gov/dailymed/druginfo.cfm?setid=8a60b0dl-2f5d-4779-895c-437aa66claal, 2 pgs.
N. T. Gregersen et al: "Acute effects of mustard, horseradish, black pepper and ginger on energy expenditure, appetite, ad libitum energy intake and energy balance in human subjects", British Journal of Nutrition, vol. 109, No. 03, Jul. 5, 2012 (Jul. 5, 2012), pp. 556-563, 8 pgs.
N Tennoune et al: "Bacterial ClpB heat-shock protein, an antigen-mimetic of the anorexigenic peptide [alpha]—MSH, at the origin of eating disorders", Translational Psychiatry, vol. 4, No. 10, Oct. 7, 2014 (Oct. 7, 2014), p. e458, 11 pgs.
Database UniProt [Online], Nov. 1, 1995 (Nov. 1, 1995), "RecName: Full=Chaperone protein ClpB1; AltName: Full=ATP-dependent Clp protease ATP-binding subunit ClpB homolog 1; AltName: Full=Casein lytic proteinase B1; AltName: Full=Heat shock protein 101; AltName: Full=Protein Defective in Long-Term Acquired Thermotolerance {ECO:0000303:PubMed:23439916};", XP002773540, retrieved from EBI accession No. UNIPROT:P42730 Database accession No. P42730 sequence, 4 pgs.
Ung Lee et al, "The *Arabidopsis* ClpB/Hsp100 family of proteins: chaperones for stress and chloroplast development *Arabidopsis* ClpB/Hsp100 proteins", The Plant Journal, vol. 49, No. 1, Nov. 28, 2006 (Nov. 28, 2006), pp. 115-127, 14 pgs.

(Continued)

*Primary Examiner* — Sudhakar Katakam
*Assistant Examiner* — Zachary J Miknis
(74) *Attorney, Agent, or Firm* — Maier & Maier, PLLC

(57) ABSTRACT

Methods of treating inflammation, in particular obesity, inducing satiation, prolonging satiety, and stimulating weight loss in a subject in need thereof, including the administration of a Brassicaceae protein extract. The Brassicaceae protein extract may be administered in the form of a dietary supplement or a food composition, either of which may include at least one additional ingredient.

17 Claims, 1 Drawing Sheet
Specification includes a Sequence Listing.

(56) References Cited

OTHER PUBLICATIONS

Schwartz et al., "Central nervous system control of food intake", 2000. Nature. 404(6778):661-71, 6 pgs.
Berthoud, "Metabolic and hedonic drives in the neural control of appetite: who is the boss?", 2011. Curr. Opin. Neurobiol. 21(6):888-896, 9 pgs.
Atasoy et al., "Deconstruction of a neural circuit for hunger", 2012. Nature. 488(7410):172-177, 9 pgs.
Garfield et al., "A neural basis for melanocortin-4 receptor-regulated appetite", 2015. Nat. Neurosci. 18(6):863-71, 12 pgs.
Carter et al., "Genetic identification of a neural circuit that suppresses appetite", 2013. Nature. 503(7474):111-114, 6 pgs.
Cone R. D., "Studies on the Physiological Functions of the Melanocortin System", 2006. Endocr. Rev. 27(7):736-49, 14 pgs.
Huszar et al., "Targeted Disruption of the Melanocortin-4 Receptor Results in Obesity in Mice", 1997. Cell. 88(1):131-41, 11 pgs.
Krude et al., "Severe early-onset obesity, adrenal insufficiency and red hair pigmentation caused by POMC mutations in humans", 1998. Nat. Genet. 19(2):155-7.
Yaswen et al., "Obesity in the mouse model of pro-opiomelanocortin deficiency responds to peripheral melanocortin", 1999. Nat. Med. 5(9):1066-70, 5 pgs.
Chen et al., "RM-493, a Melanocortin-4 Receptor (MC4R) Agonist Increases Resting Energy Expenditure in Obese Individuals", 2015. J. Clin. Endocrinol. Metab. 100(4):1639-45, 8 pgs.
Kühnen et al., "Proopiomelanocortin Deficiency Treated with a Melanocortin-4 Receptor Agonist", 2016. N. Engl. J. Med. 375(3):240-6, 7 pgs.
Mul et al., "Melanocortin MC4 receptor-mediatedfeedingand groominginrodents", 2013. Eur. J. Pharmacol. 719(1-3):192-20, 10 pgs.
Panaro et al., "The Melanocortin-4 Receptor Is Expressed in Enteroendocrine L Cells and Regulates the Release of Peptide YY and Glucagon-like Peptide 1 In Vivo", 2014. Cell Metab. 20(6):1018-1029, 12 pgs.
Brzoska et al., "α-Melanocyte-Stimulating Hormone and Related Tripeptides: Biochemistry, Antiinflammatory and Protective Effects in Vitro and in Vivo, and Future Perspectives for the Treatment of Immune-Mediated Inflammatory Diseases", 2008. Endrocr. Rev. 29(5):581-602, 22 pgs.
Auriemma et al, "α-MSH-Stimulated Tolerogenic Dendritic Cells Induce Functional Regulatory T Cells and Ameliorate Ongoing Skin Inflammation", 2012. J. Invest. Dermatol. 132(7):1814-24, 11 pgs.
Kleiner et al., "Regulation of melanocortin 1 receptor in allergic rhinitis in vitro and in vivo", Clin. Exp. Allergy. 46(8):1066-74, 9 pgs.
Böhm et al., "α-MSH modulates cell adhesion and inflammatory responses of synovial fibroblasts from osteoarthritis patients", 2016. Biochem. Pharmacol. 116:89-99, 11 pgs.
Mykicki et al., "Melanocortin-1 receptor activation is neuroprotective in mouse models of neuroinflammatory disease", 2016. Sci. Transl. Med. 8(362):362ra146, 17 pgs.
Murphy et al., "Gut hormones and the regulation of energy homeostasis", 2006. Nature. 444(7121):854-859, 6 pgs.

\* cited by examiner

```
                       1                 13
α-MSH                 SYSME HFRW GKPV
                          |   || | ||
SEQ ID NO:1           EHIAEVVSRWTGIPV
                     535               549
```

BRASSICACEAE PROTEIN EXTRACT AND USES THEREOF

FIELD

The present invention relates to the field of health and welfare. In particular, the present invention relates to methods of treating inflammation and stimulating weight loss in a subject in need thereof.

BACKGROUND

There is an increasing concern with personal weight and appearance. Diets and weight loss programs are extensively advertised that have varying degrees of effectiveness, and utilized by a large segment of Western society, even by persons with weights in the normal range. There is, therefore, a continuing search for new and effective means to facilitate weight loss.

Obesity on the other hand is one of such poorly treatable chronic conditions accompanied by numerous comorbidities. Obesity and overweight are typically characterized by increased food intake and decreased energy expenditure suggesting altered role of peptidergic systems regulating energy balance. Indeed, the regulation of appetite and feeding behavior involves interaction between intestinal hunger and satiety peptide hormones with the brain neuronal circuitries containing orexigenic and anorexigenic neuropeptides (Schwartz et al., 2000. Nature. 404(6778):661-71).

The current model of food intake control implicates gut-derived hunger and satiety hormones signalling to several brain circuitries regulating homeostatic and hedonic aspects of feeding (Berthoud, 2011. Curr. Opin. Neurobiol. 21(6):888-896; Murphy et al., 2006. Nature. 444(7121):854-859). Prominent amongst these are the anorexigenic and orexigenic pathways originating from the hypothalamic arcuate nucleus (ARC) that include the proopiomelanocortin (POMC) and neuropeptide Y (NPY)/agouti-related protein (AgRP) neurons, respectively, relayed in the paraventricular nucleus (PVN) (Atasoy et al., 2012. Nature. 488(7410):172-177; Garfield et al., 2015. Nat. Neurosci. 18(6):863-71). The ARC and PVN pathways converge in the lateral parabrachial nucleus which sends anorexigenic projections to the central amygdala (CeA), expressing calcitonin gene-related peptide (CGRP) (Carter et al., 2013. Nature. 503(7474):111-114).

The central melanocortin (MC) system consisting of melanocortin peptides including α-melanocyte-stimulating hormone (α-MSH) derived from its precursor proopiomelanocortin (POMC) and acting on the MC type 4 receptors (MC4R) is critically involved in regulation of energy balance (Cone R. D., 2006. Endocr. Rev. 27(7):736-49). In fact, deficit in both POMC expression and MC4R signalling leads to hyperphagia and obesity in both human and genetically modified rodents (Huszar et al., 1997. Cell. 88(1):131-41; Krude et al., 1998. Nat. Genet. 19(2):155-7; Yaswen et al., 1999. Nat. Med. 5(9):1066-70). Selective stimulation of the central MC4R appears hence as a very attractive target to treat hyperphagia and obesity and several α-MSH peptide analogues have been developed and clinically tested, such as for instance setmelanotide as a replacement therapy during POMC deficiency and for treatment hyperphagia in Prader-Willi syndrome (Chen et al., 2015. J. Clin. Endocrinol. Metab. 100(4):1639-45; Kühnen et al., 2016. N. Engl. J. Med. 375(3):240-6).

A search for non-brain penetrating α-MSH-like drugs acting on peripheral MCR may represent an alternative strategy for body weight management. In fact, MC4R are expressed in both the peripheral nervous system and in the intestinal enteroendocrine cells. Although MC4R-mediated α-MSH anorexigenic effects have been mainly ascribed to its central sites of actions (Mul et al., 2013. Eur. J. Pharmacol. 719(1-3):192-20), a recent study showed that activation of the MC4R in the gut enteroendocrine cells stimulates release of satiety hormones glucagon-like peptide-1 (GLP-1) and peptide YY (PYY) (Panaro et al., 2014. Cell Metab. 20(6):1018-1029). Thus, α-MSH-like molecules may act as a peripheral satiety signal upstream to the brain anorexigenic pathways.

The hormone α-MSH is also known to have potent anti-inflammatory effects and protective effects on cells of the immune system and on peripheral nonimmune cell types expressing melanocortin receptors, such as MC1R and MC3R (Brzoska et al., 2008. Endrocr. Rev. 29(5):581-602). Moreover, recent studies show that α-MSH is an interesting target for treating psoriasis, allergic rhinitis, osteoarthritis and neuroinflammatory diseases (Auriemma et al, 2012. J. Invest. Dermatol. 132(7):1814-24; Kleiner et al., Clin. Exp. Allergy. 46(8):1066-74; Böhm et al., 2016. Biochem. Pharmacol. 116:89-99; Mykicki et al., 2016. Sci. Transl. Med. 8(362):362ra146).

The inventors have surprisingly identified Brassicaceae proteins having sequence homology with α-MSH. Therefore, the present invention relates to a Brassicaceae protein extract and uses thereof.

SUMMARY

The present invention relates to the use of a Brassicaceae protein extract or derivative thereof for use for stimulating weight loss in a subject in need thereof.

The present invention also relates to the use of a Brassicaceae protein extract or derivative thereof for use for reducing weight gain in a subject in need thereof.

The present invention further relates to the use of a Brassicaceae protein extract or derivative thereof for use for inducing satiation in a subject in need thereof.

In one embodiment, the Brassicaceae is a *Brassica* species.

In one embodiment, the *Brassica* species is selected from the group comprising *Brassica oleracea, Brassica rapa, Brassica napus, Brassica nigra, Brassica carinata, Brassica juncea, Raphanus sativus, Armoracia rusticana, Matthiola* and *Arabidopsis thaliana*.

In one embodiment, the Brassicaceae protein extract or derivative thereof according to the invention comprises at least 10% by weight of proteins, preferably at least 20%, more preferably at least 30%.

In one embodiment, the Brassicaceae protein extract or derivative thereof according to the invention comprises fibers, wherein the ratio proteins/fibers in weight is of at least 2.5, preferably at least 3.

In one embodiment, the subject is not obese. In another embodiment, the subject is obese. In another embodiment, the subject is overweight.

In one embodiment, the Brassicaceae protein extract or derivative thereof according to the invention is administered to the subject in the form of a dietary supplement or food composition.

In one embodiment, the dietary supplement or food composition of the invention further comprises at least one additional ingredient selected from the group comprising simple and/or complex carbohydrates, lipids, fibers, minerals or mixture thereof.

In one embodiment, the Brassicaceae protein extract or derivative thereof according to the invention is administered to the subject orally.

In one embodiment, the Brassicaceae protein extract or derivative thereof according to the invention is administered simultaneously or sequentially with one meal of the subject.

Another object of the present invention relates to a kit comprising a Brassicaceae protein extract or derivative thereof as described herein, and optionally means to administer said Brassicaceae protein extract or derivative thereof a subject in need thereof.

DETAILED DESCRIPTION

Figures 1, 2:
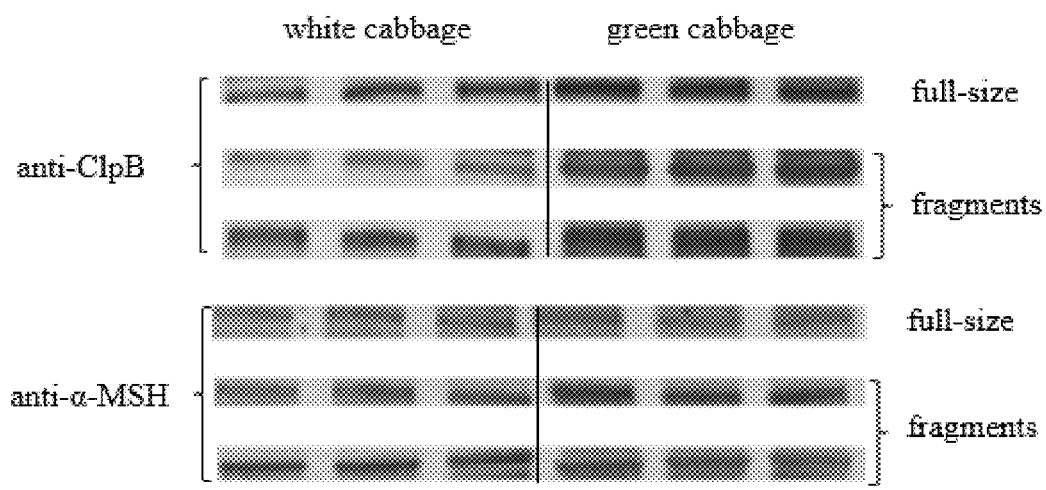
FIG. 1 is a sequence alignment showing similarity between the human α-MSH sequence and the ClpB sequence of Brassicaceae.
FIG. 2 is a set of photographs showing western blot on protein extracts of white cabbage and green cabbage using anti-ClpB (top) or anti-α-MSH (bottom) antibodies. Full-size ClpB (~95 kDa) and fragments of ClpB are indicated. Each experiment was repeated 3 times.

In the present invention, the following terms have the following meanings:

"About" preceding a figure means plus or less 10% of the value of said figure.

"Binge eating", "compulsive eating", "binge eating disorder" and "compulsive eating disorder" refer to an eating disorder consisting of episodes of uncontrollable eating, but without subsequent purging episodes (e.g., vomiting). "Binge eaters" are identified as experiencing binge- or compulsive eating based upon a Binge Eating Scale checklist (Gormally et al., 1982. Addict Behav. 7(1):47-55) or an equivalent diagnostic measure (e.g., professional assessment). Binge or compulsive eating severity is measured by the severity of individual events and/or by the frequency of such events.

"Cabbage family" has its general meaning in the art and refers to the Brassicaceae family, also known as Cruciferae, crucifers or mustards. The Brassicaceae family comprises over 300 genera, including, but not limited to, *Aethionema, Agallis, Alliaria, Alyssoides, Alyssopsis, Alyssum, Anastatica, Anelsonia, Arabidopsis, Arabis, Armoracia, Athysanus, Aubrieta, Aurinia, Ballantinia, Barbarea, Biscutella, Boechera, Brassica, Braya, Bunias, Cakile, Camelina, Capsella, Cardamine, Cardaria, Caulanthus, Caulostramina, Cheesemania, Cheiranthus, Chorispora, Clypeola, Cochlearia, Coincya, Coluteocarpus, Conringia, Coronopus, Crambe, Cusickiella, Degenia, Descurainia, Diplotaxis, Dithyrea, Draba, Drabastrum, Eruca, Erucaria, Erucastrum, Erysimum, Euclidium, Eudema, Farsetia, Fibigia, Galitzkya, Glaucocarpum, Goldbachia, Graellsia, Guillenia, Halimolobos, Heliophila, Hemicrambe, Hesperis, Heterodraba, Hirschfeldia, Hornungia, Hugueninia, Iberis, Idahoa, Ionopsidium, Isatis, Lachnocapsa, Leavenworthia, Lepidium, Lobularia, Lunaria, Malcolmia, Maresia, Matthiola, Microstigma, Moricandia, Nasturtium, Neslia, Nesocrambe, Orychophragmus, Pachycladon, Pachymitus, Parolinia, Paysonia, Pegaeophyton, Peltaria, Petroravenia, Phlebolobium, Phoenicaulis, Physaria, Physoptychis, Polyctenium, Pringlea, Raphanus, Rapistrum, Rhammatophyllum, Roripella, Schivereckia, Schizopetalon, Sibara, Sibaropsis, Sinapis, Sisymbrium, Solms-laubachia, Stanleya, Streptanthella, Streptanthus, Subularia, Tauscheria, Teesdalia, Thellungiella, Thelypodium, Thlaspi, Thysanocarpus, Tropidocarpum, Turritis, Vella, Zerdana* and *Zilla*. Among the best known, the Brassicaceae family comprises the cruciferous vegetables, including species such as *Brassica oleracea* (e.g., broccoli, cabbage, cauliflower, kale, collards), *Brassica rapa* (turnip, Chinese cabbage, etc.), *Brassica napus* (rapeseed, etc.), *Raphanus sativus* (common radish), *Armoracia rusticana* (horseradish), *Matthiola* (stock) and the model organism *Arabidopsis thaliana* (thale cress).

"Conformational mimetic" refers to a polypeptide or protein that shares at least in part the same conformation as another protein. In one embodiment, a "conformational mimetic of the α-MSH peptide" means a polypeptide or protein that shares at least in part the same conformation as the α-MSH peptide. In a particular embodiment, a conformational mimetic of the α-MSH peptide has, from N-terminal to C-terminal, a negatively charged residue, consecutive Arg and Trp residues, and/or a sequence having at least 75% sequence homology with the sequence GKPV.

"Dietary supplement" refers to a product taken by mouth that contains a dietary ingredient intended to supplement the diet.

"Essential amino acid" refers to an amino acid which is synthesized only by plants or microorganisms or which is not produced by animals, preferably by humans, in sufficient quantities to support normal growth and development. Essential amino acids include, but are not limited to, histidine, isoleucine, leucine, lysine, methionine, phenylalanine, threonine, tryptophan and valine.

"Extract" refers to an extract wherein more than 90% of the solvent has been removed, preferably more than 95%, that is an extract that comprises less than 10%, preferably less than 5% residual solvent.

"Food composition" refers to any substance containing nutrients, whether for human or animal consumption, whether comprised of a single ingredient or a mixture of ingredients, whether liquid, liquid containing or solid, whether primarily carbohydrate, fat, protein or any mixture thereof, whether edible per se or requiring processing like cooking, mixing, cooling, mechanical treatment and the like.

"Fragment" refers to a part or a region of a protein, e.g., of the ClpB protein, comprising fewer amino acid residues than an intact or complete protein, e.g., the ClpB protein. The term "fragment" further refers to, for example, an at least about 5, 10, 20, 30, 40, 50, 75, 100, 150, 200, 250, 300, 400, 500, 600, 700, 800 or more amino acid portion of an amino acid sequence, e.g., of amino acid sequence SEQ ID NO: 1, which portion is cleaved from a naturally occurring amino acid sequence by proteolytic cleavage by at least one protease, or is a portion of the naturally occurring amino acid sequence synthesized by chemical methods or using recombinant DNA technology (e.g., expressed from a portion of the nucleotide sequence encoding the naturally occurring amino acid sequence) known to one of skill in the art. "Fragment" may also refer to a portion, for example, of about 5%, about 10%, about 20%, about 30%, about 40%, about 50%, about 60%, about 70%, about 80% about 90% about 95% or about 99% of a particular amino acid sequence, e.g., of amino acid sequence SEQ ID NO: 1.

The term "fragment" further includes, but is not limited to, truncation polypeptides having the amino acid sequence of the ClpB protein, except for deletion of a continuous series of residues that includes the amino terminus, or a continuous series of residues that includes the carboxyl terminus or deletion of two continuous series of residues, one including the amino terminus and one including the carboxyl terminus.

Preferably, fragments of the invention are characterized by structural or functional attributes such as fragments that comprise alpha-helix and alpha-helix forming regions, beta-sheet and beta-sheet forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

The term "fragment" also refers to biologically active fragments. Biologically active fragments are those that mediate ClpB protein activity, including those with a similar activity or an improved activity, or with a decreased undesirable activity. Also included are those that antigenic or immunogenic in an animal or in a human.

"Identity" or "identical", when used in a relationship between the sequences of two or more amino acid sequences, refers to the degree of sequence relatedness between amino acid sequences, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Methods for comparing the identity of two or more sequences are well known in the art. Such methods include, but are not limited to, those described in Arthur M. Lesk, *Computational Molecular Biology: Sources and Methods for Sequence Analysis* (New-York: Oxford University Press, 1988); Douglas W. Smith, *Biocomputing: Informatics and Genome Projects* (New-York: Academic Press, 1993); Hugh G. Griffin and Annette M. Griffin, *Computer Analysis of Sequence Data, Part 1* (New Jersey: Humana Press, 1994); Gunnar von Heinje, *Sequence Analysis in Molecular Biology: Treasure Trove or Trivial Pursuit* (Academic Press, 1987); Michael Gribskov and John Devereux, *Sequence Analysis Primer* (New York: M. Stockton Press, 1991); and Carillo et al., 1988. *SIAM J. Appl. Math.* 48(5):1073-1082. Preferred methods for determining identity are designed to give the largest match between the sequences tested. Methods of determining identity are described in publicly available computer programs. Computer program methods for determining identity between two sequences include the GCG program package, including GAP (Devereux et al., 1984. *Nucl. Acid. Res.* 12(1 Pt 1):387-395; Genetics Computer Group, University of Wisconsin Biotechnology Center, Madison, Wis.), BLASTP, BLASTN, TBLASTN and FASTA (Altschul et al., 1990. *J. Mol. Biol.* 215(3): 403-410). The BLASTX program is publicly available from the National Center for Biotechnology Information (NCBI) and other sources (BLAST Manual, Altschul et al. NCB/NLM/NIH Bethesda, Md. 20894; Altschul et al., 1990. *J. Mol. Biol.* 215(3):403-410). The "needle" program, which uses the Needleman-Wunsch global alignment algorithm (Needleman S B and Wunsch C. D., 1970. *J. Mol. Biol.* 48: 443-453) to find the optimum alignment (including gaps) of two sequences when considering their entire length, may preferably be used. The needle program is, for example, available on the ebi.ac.uk world wide web site. The percentage of identity in accordance with the invention is preferably calculated using the EMBOSS: needle (global) program with a "Gap Open" parameter equal to 10.0, a "Gap Extend" parameter equal to 0.5, and a Blosum62 matrix. The well-known Smith Waterman algorithm may also be used to determine identity.

"Obesity" refers to a medical condition wherein the subject preferably has a BMI of >30. The "BMI" or "body mass index" is defined as the subject's body mass divided by the square of his height. The formulae universally used in medicine produces a unit of measure of $kg/m^2$. A "moderately obese" subject refers to a subject having a BMI of between 30 and 35. A "non-obese" subject has a BMI<30. In one embodiment, a "non-obese" subject has normal body weight. In another embodiment, a "non-obese" subject is an overweight subject. "Normal body weight" refers herein to body weight resulting in a BMI of between 18.5 and 25.

"Overweight" refers to body weight resulting in a BMI of between 25 and 30. In some embodiments, the subject is a healthy overweight or uncomplicated overweight subject. By "healthy overweight" or "uncomplicated overweight" subject is meant herein an overweight subject who does not display any disease or condition directly associated with his/her weight.

"Pharmaceutically" or "pharmaceutically acceptable" refer to molecular entities and compositions that do not produce an adverse, allergic or other untoward reaction when administered to a subject, especially a human, as appropriate. A pharmaceutically acceptable carrier or excipient refers to a non-toxic solid, semi-solid or liquid filler, diluent, encapsulating material or formulation auxiliary of any type. Pharmaceutically acceptable excipients that may be used in the compositions of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (for example sodium carboxymethylcellulose), polyethylene glycol, polyacrylates, waxes, polyethylene-polyoxypropylene-block polymers, polyethylene glycol and wool fat. In the pharmaceutical compositions of the present invention, the active ingredient as below, alone or in combination with another active ingredient, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, intrathecal and intranasal administration forms and rectal administration forms. Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The active ingredient can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatine. Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion. Some variation in dosage will necessarily occur depending on the condition of the subject being treated. The person responsible for administration will, in any event, determine the appropriate dose for the individual subject.

"Polypeptide" is used in its conventional meaning, i.e., as a sequence of less than 100 amino acids. A polypeptide usually refers to a monomeric entity. The term "protein" refers to a sequence of more than 100 amino acids and/or to a multimeric entity. The proteins of the invention are not limited to a specific length of the product. This term does not refer to or exclude post-expression modifications of the protein, for example, glycosylation, acetylation, phosphorylation and the like, as well as other modifications known in the art, both naturally occurring and non-naturally occurring. A protein may be an entire protein, or a subsequence thereof.

"Polypeptide derivative" refers to compound having an amino group (—NH—), and more particularly, a peptide bond. Polypeptides may be regarded as substituted amides. Like the amide group, the peptide bond shows a high degree of resonance stabilization. The C—N single bond in the peptide linkage has typically about 40 percent double-bond character and the C=O double bond about 40 percent single-bond character. "Protecting groups" are those groups that prevent undesirable reactions (such as proteolysis) involving unprotected functional groups. Specific examples of amino protecting groups include formyl; trifluoroacetyl; benzyloxycarbonyl; substituted benzyloxycarbonyl such as (ortho- or para-) chlorobenzyloxycarbonyl and (ortho- or para-) bromobenzyloxycarbonyl; and aliphatic oxycarbonyl such as t-butoxycarbonyl and t-amiloxycarbonyl. The carboxyl groups of amino acids can be protected through conversion into ester groups. The ester groups include benzyl esters, substituted benzyl esters such as methoxybenzyl ester; alkyl esters such as cyclohexyl ester, cycloheptyl ester or t-butyl ester. The guanidino moiety may be protected by nitro; or arylsulfonyl such as tosyl, methoxybenzensulfonyl or mesitylenesulfonyl, even though it does not need a protecting group. The protecting groups of imidazole include tosyl, benzyl and dinitrophenyl. The indole group of tryptophan may be protected by formyl or may not be protected.

The modification of the ClpB protein, fragment or variant thereof of the invention aims in particular to improve their life time in vivo. One type of modification is the addition to the N or C termini of the protein or peptide of polyethylene glycol (PEG). PEG is known by the person skilled in the art to have many properties that make it an ideal carrier for polypeptides such as high water solubility, high mobility in solution and low immunogenicity. This modification also protects the polypeptides from exopeptidases and therefore increases their overall stability in vivo.

The other modifications used to prevent degradation of polypeptides by endopeptidases or exopeptidases include N-terminal modifications such as acetylation or glycosylation, C-terminal modifications such as amidation and use of unnatural amino acids (β-amino and α-trifluoromethyl amino acids) at particular sites within the polypeptides or proteins.

Another alternative to increase polypeptide molecular size is the genetic fusion of the polypeptides to the Fc domain of human immunoglobulin (including, for example, IgA, IgM and IgG) or the fusion of the polypeptides to albumin "Protein extract" refers to partial or total proteins extracted from a plant part, preferably form a plant of the Brassicaceae family Plant protein extraction methods are well known in the art.

"Satiety" refers to an essentially homeostatic state wherein an individual feels that their cravings are satisfied or minimized Many physiological factors are believed to bear on an individual's satiety. For instance, gustation, or taste, olfaction, or smell, as well as a feeling of fullness of the stomach may all contribute to whether an individual feels "satiated." More in particular, "satiety" is the state in which further eating is inhibited and determines the time between meals and the amount of food consumed at the next meal. An "enhanced feeling of satiety" or the like, this has the meaning of the feeling of satiety being more pronounced and/or more prolonged compared to a control situation.

"Satiation" refers to the state which terminates eating within a meal, typically occurring/observed within a period (e.g. 20-30 min) after the start of consuming the meal. Thus, whenever reference is made in this document to "inducing satiation" or the like, this has the meaning of arousing the tendency of a subject to stop consuming food during a meal. The effect on satiation can be determined by scoring the time point of meal termination from the time point of meal beginning, i.e., the time elapsed between meal start and meal termination. A satiation effect is seen if the amount of consumed calories at meal termination is significantly less than in the controls, such as for example at least 1%, 2%, 3%, 4%, 5%, 10% 20%, or more. Over a longer time period (such as 1, 2, 3, 4, 5 weeks or more), one can also score the body weight reduction or the body weight change compared to a control diet. Body weight of a subject being administered regular amounts of the test compositions (e.g. once daily, twice daily, or more) is preferably significantly controlled (reduced or less increased) compared to the control subjects. As used herein, the "control subject" refers to the subjects who were not administered with the ClpB protein, fragment or variant thereof of the present invention.

"Subject" refers to a warm-blooded animal, preferably a human, a pet or livestock. As used herein, the terms "pet" and "livestock" include, but are not limited to, dogs, cats, guinea pigs, rabbits, pigs, cattle, sheep, goats, horses and poultry. In some embodiments, the subject is a male or female subject. In some embodiments, the subject is an adult (for example, a subject above the age of 18 (in human years) or a subject after reproductive capacity has been attained). In another embodiment, the subject is a child (for example, a subject below the age of 18 (in human years) or a subject before reproductive capacity has been attained). In some embodiments, the subject may be a "patient", i.e., a subject who/which is awaiting the receipt of, or is receiving medical care or was/is/will be the object of a medical procedure, such as a medical procedure according to the methods of the present invention, or is monitored for the development of a disease.

"Sustained release" indicates that the therapeutically active agent may be released from the composition at a controlled rate in such a manner that blood levels (that are still below the toxic levels of the medicament) may be maintained at therapeutically beneficial levels over an extended duration of time (e.g., 24 hours or more, thereby providing a single dose, daily dosage formulation).

"Therapeutically effective amount" refers to a quantity of protein extract or derivative thereof sufficient to, without causing significant negative or adverse side effects to the subject, achieve the beneficial effect (e.g. stimulating satiety, prolonging satiation, reducing food intake, controlling, in particular reducing, weight gain, stimulating weight loss, and/or reducing fat mass on lean mass ratio). In the context of the present invention, the amount of protein extract or derivative thereof administered to the subject will depend on the characteristics of the individual, such as general health, age, sex, body weight . . . . The skilled artisan will be able to determine appropriate dosages depending on these and other factors.

"Treating", "treatment" or "alleviation" refer to both therapeutic treatment and prophylactic or preventative measures; wherein the object is to prevent or slow down (lessen) the targeted condition or disorder. Those in need of treatment include those already with the disorder as well as those prone to have the disorder or those in whom the disorder is to be prevented. A subject or mammal is successfully "treated" for the targeted condition or disorder if, after receiving a therapeutic amount of an agent according to the present invention, the subject shows observable and/or measurable: satiation, prolonged satiety, reduced food intake, controlled weight gain, stimulated weight loss and/or reduced fat mass on lean mass ratio. These parameters for assessing successful treatment and improvement in the condition or disorder are readily measurable by routine procedures familiar to a physician.

The present invention relates to a Brassicaceae protein extract and uses thereof.

As used herein, the term "Brassicaceae protein extract" means a mixture comprising at least one protein obtained from a plant of the Brassicaceae family.

Techniques to obtain protein extracts from vegetables are well-known from the one skilled in the art.

In one embodiment, the protein extract of the invention is a protein extract of a *Brassica* species selected from the group comprising or consisting of *Brassica oleracea, Brassica rapa, Brassica napus, Brassica nigra, Brassica carinata, Brassica juncea, Raphanus sativus, Armoracia rusticana, Matthiola* and *Arabidopsis thaliana*.

Accordingly, in one embodiment, the Brassicaceae protein extract of the invention is a *Brassica* protein extract selected from the group comprising or consisting of protein extracts of *Brassica oleracea, Brassica rapa, Brassica napus, Brassica nigra, Brassica carinata, Brassica juncea, Raphanus sativus, Armoracia rusticana, Matthiola* and *Arabidopsis thaliana*.

In one embodiment, the protein extract of the invention is a protein extract of a *Brassica* selected from the group comprising or consisting of cabbage (such as white cabbage, green cabbage, red cabbage), broccoli, cauliflower, kale, Brussels sprouts, collard greens, savoy, kohlrabi, gai lan, bok choy, bomdong, choy sum, field mustard, komatsuna, napa cabbage, rapini, tatsoi, turnip, yellow sarson, rapeseed, canola, rutabagas, Siberian kale, Hanover salad and thale cress.

Accordingly, in one embodiment, the Brassicaceae protein extract of the invention is a *Brassica* protein extract selected from the group comprising or consisting of protein extracts of cabbage (such as white cabbage, green cabbage, red cabbage), broccoli, cauliflower, kale, Brussels sprouts, collard greens, savoy, kohlrabi, gai lan, bok choy, bomdong, choy sum, field mustard, komatsuna, napa cabbage, rapini, tatsoi, turnip, yellow sarson, rapeseed, canola, rutabagas, Siberian kale, Hanover salad and thale cress.

In a particular embodiment, the Brassicaceae protein extract of the invention is a protein extract of *Brassica oleracea, Brassica rapa, Brassica napus* or *A. thaliana*.

In one embodiment, the Brassicaceae protein extract of the invention is a protein extract of *A. thaliana* such as thale cress.

In one embodiment, the Brassicaceae protein extract of the invention is a protein extract of a plant species selected from the group comprising or consisting of *Brassica oleracea, Brassica rapa* and *Brassica napus*.

In one embodiment, the Brassicaceae protein extract of the invention is a protein extract of *Brassica oleracea* such as cabbage (such as white cabbage, green cabbage, red cabbage), broccoli, cauliflower, kale, Brussels sprouts, collard greens, savoy, kohlrabi and gai lan.

In one embodiment, the Brassicaceae protein extract of the invention is a protein extract of *Brassica rapa* such as bok choy, bomdong, choy sum, field mustard, komatsuna, napa cabbage, rapini, tatsoi, turnip and yellow sarson.

In one embodiment, the Brassicaceae protein extract of the invention is a protein extract of *Brassica napus* such as rapeseed, canola, rutabagas, Siberian kale and Hanover salad.

In one embodiment, the Brassicaceae protein extract is obtained from at least one portion of the respective vegetable or plant. In particular, the vegetable or plant portion from which the at least one plant extract is obtained include, but are not limited to, leaves, bark, roots, rootstocks, stem, seeds and/or flowers, in accordance with the characteristics of the plant extract that one wishes to obtain or with the particular characteristics of the vegetable or plant, also in accordance with the plant portions in which the active ingredients, which are desired to be present in the at least one plant extract, are contained.

In one embodiment, the protein extract of the invention comprises at least about 10% by weight of proteins. In a particular embodiment, the protein extract of the invention comprises at least about 11, 12, 13, 14, 15, 16, 17, 18, 19 or 20% by weight of proteins.

In another embodiment, the protein extract of the invention comprises at least about 25, 30, 35, 40 or 45% by weight of proteins. In another embodiment, the protein extract of the invention comprises at least about 50% by weight of proteins. In another embodiment, the protein extract of the invention comprises at least about 55, 60, 65, 70, 75, 80, 85, 90, 95, 99% or more by weight of proteins.

In one embodiment, the protein extract of the invention essentially comprises proteins.

In one embodiment, the protein extract of the invention comprises from about 10 to about 99% by weight of proteins, preferably from about 20 to about 95%, more preferably from about 30 to about 90%. In another embodiment, the protein extract of the invention comprises from about 40 to about 99% by weight of proteins, preferably from about 50 to about 95%, more preferably from about 60 to about 90%.

In one embodiment, the protein extract of the present invention comprises the ClpB protein. As an illustration for example, in one embodiment, the protein extract of the present invention is a protein extract of *A. thaliana* and comprises the ClpB protein having the amino acid sequence SEQ ID NO:1, fragment or variant thereof. In one embodiment, the protein extract of the present invention comprises a ClpB protein having at least 70% identity with the amino acid sequence SEQ ID NO:1. In another embodiment, the protein extract of the present invention comprises a ClpB protein having at least 75%, 80%, 85%, 90%, 91%, 92%, 93%, 94%, 95%, 96%, 97%, 98%, 99%, or 100% identity with the amino acid sequence SEQ ID NO:1.

In one embodiment, the protein extract of the invention comprises less than about 30% by weight of fibers. In a particular embodiment, the protein extract of the invention comprises less than about 25, 20, 15 or 10% by weight of fibers. In a particular embodiment, the protein extract of the invention comprises less than about 9, 8, 7, 6, 5, 4, 3, 2 or 1% by weight of fibers.

In one embodiment, the protein extract of the invention is substantially free of fibers. Accordingly, in one embodiment, the protein extract of the invention does not comprise fibers.

In one embodiment, the protein extract of the invention comprises proteins and fibers, wherein the ratio proteins/fibers in weight is at least 2. Accordingly, in one embodiment, the protein extract of the invention comprises at least two-fold more proteins than fibers.

In one embodiment, the ratio proteins/fibers in weight of the protein extract of the invention is at least 2.5, 3, 3.5, 4, 4.5, 5, 6, 7, 8, 9, 10 or more. In one embodiment, the ratio proteins/fibers in weight of the protein extract of the invention ranges from 2 to 20, from 2 to 18, from 2 to 15 or from 2 to 10.

In one embodiment, the Brassicaceae protein extract according to the present invention is in the form of a liquid, such as aqueous and non-aqueous solutions; a solid; or a powder, such as micronized powder, lyophilized powder or wet powder; and the like.

In a particular embodiment, the Brassicaceae protein extract according to the present invention is in the form of anhydrous powder or powder containing water or moisture.

In one embodiment, the protein extract of the invention may be in the form of a derivative.

In one embodiment, the protein extract of the invention can have the same division into amino acids as the non-derived extract, optionally with lower molar masses.

In one embodiment, "Brassicaceae protein extract derivative" or "Brassicaceae protein extract in the form of a derivative" or "derived Brassicaceae protein extract" or "derived Brassicaceae protein" designates a product which can be obtained by chemical modification of the molecules of the Brassicaceae protein extract.

In other words, in one embodiment, a derived Brassicaceae protein extract is a protein extract comprising groups which are the same or different and are grafted covalently onto amino acid functional groups contained in the protein extract, and/or a hydrolysed Brassicaceae protein extract.

Without a limitation to any one theory, chemical groups can be grafted specifically onto the —OH or —NH2 or —COOH functional groups carried on the side chains of amino acids and/or the terminal functional groups of proteins.

In one embodiment, chemical groups which can be grafted onto the amino acids in the protein extract include cationic or cationisable groups; anionic or anionisable groups; uncharged hydrophilic or hydrophobic groups; groups cross-linking the guar protein extract, optionally polymeric groups; and combinations thereof.

By "cationisable groups" are meant groups which are potentially cationic, i.e. which can become cationic depending on the pH of the medium. By "anionisable groups" are meant groups which are potentially anionic, i.e. which can become anionic depending on the pH of the medium.

Another object of the present invention is a dietary supplement or protein dietary supplement comprising the Brassicaceae protein extract or derivative thereof, and uses thereof.

Another object of the present invention is a food composition comprising the Brassicaceae protein extract or derivative thereof, and uses thereof.

In one embodiment, the Brassicaceae protein extract or derivative thereof according to the invention is administered, is to be administered or is adapted to be administered in the form of a dietary supplement. In one embodiment, the Brassicaceae protein extract or derivative thereof according to the invention is administered, is to be administered or is adapted to be administered in the form of a food composition.

In one embodiment, the dietary supplement or food composition comprises or consists of at least about 10% by weight or more of the Brassicaceae protein extract or derivative thereof according to the invention. In one embodiment, the dietary supplement or food composition comprises or consists of at least about 15%, 20%, 25%, 30%, 40%, 50%, 60%, 70%, 80% by weight or more of the Brassicaceae protein extract or derivative thereof according to the invention.

In one embodiment, the dietary supplement or food composition of the present invention comprises at least one additional ingredient selected from the group comprising or consisting simple and/or complex carbohydrates, lipids, fibers, minerals or mixture thereof. In a particular embodiment, the dietary supplement or food composition of the present invention further comprises fibers.

In one embodiment, the dietary supplement or food composition of the present invention comprises at least one essential amino acid. Preferably, said at least one essential amino acid is isolated or free, i.e., not bonded in a protein chain.

In one embodiment, the dietary supplement or food composition further comprises carriers or vehicles. "Carriers" or "vehicles" mean materials suitable for administration and include any such material known in the art such as, for example, any liquid, gel, solvent, liquid diluent, solubilizer, or the like, which is non-toxic and which does not interact with any components, in particular with the bacterial strain, of the composition in a deleterious manner Examples of nutritionally acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

In one embodiment, the dietary supplement or food composition of the present invention comprises dietary fibers. Dietary fibers pass through the small intestine undigested by enzymes and functions as a natural bulking agent and laxative. Dietary fibers may be soluble or insoluble and in general a blend of the two types is preferred. Suitable sources of dietary fibers include soy, pea, oat, pectin, guar gum, gum Arabic, fructooligosaccharides, galacto-oligosaccharides, sialyl-lactose and oligosaccharides derived from animal milks. In some embodiments, the dietary fiber is selected among mannans. Mannans (such as glucomannans and galactomannans), such as guar gum, locust bean gum, konjac, and xanthan gum, are present in some plant cell walls. The glucomannans are generally comprised of (1-4)-β-linked glucose and mannose units, while the galactomannans are generally comprised of a (1-4)-β-mannan backbone substituted with single units of (1-6)-α-galactose. Many endospermic legumes, such as guar and locust bean, contain galactomannans in the endosperm during seed development. Glucomannans have also been found as a minor component of cereal grains.

In one embodiment, the dietary supplement or food composition of the present invention comprises minerals and micronutrients such as trace elements and vitamins in accordance with the recommendations of Government bodies such as the USRDA. For example, the composition may comprise per daily dose one or more of the following micronutrients in the ranges given: 300 to 500 mg calcium, 50 to 100 mg magnesium, 150 to 250 mg phosphorus, 5 to 20 mg iron, 1 to 7 mg zinc, 0.1 to 0.3 mg copper, 50 to 200 µg iodine, 5 to 15 µg selenium, 1000 to 3000 µg beta carotene, 10 to 80 mg Vitamin C, 1 to 2 mg Vitamin B1, 0.5 to 1.5 mg Vitamin B6, 0.5 to 2 mg Vitamin B2, 5 to 18 mg niacin, 0.5 to 2.0 µg Vitamin B12, 100 to 800 µg folic acid, 30 to 70 µg biotin, 1 to 5 µg Vitamin D, 3 to 10 µg Vitamin E.

In one embodiment, the dietary supplement or food composition of the present invention further comprises emulsifiers. Examples of food grade emulsifiers typically include diacetyl tartaric acid esters of mono- and di-glycerides, lecithin and mono- and di-glycerides. Similarly, suitable salts and stabilisers may be included.

In one embodiment, the dietary supplement or food composition according to the present invention can be used for the preparation of dietary food.

In one embodiment, the dietary supplement or food composition according to the present invention can be used for introduction into daily meals.

In one embodiment, the dietary supplement according to the present invention is in the form of a powder, such as micronized powder, lyophilized powder or wet powder; aqueous and non-aqueous solutions; and the like.

In one embodiment, the dietary supplement according to the present invention is in the form of anhydrous powder or powder containing water or moisture. In one embodiment, the dietary supplement or food composition according to the present invention is in the form of liquid.

In one embodiment, the food composition of the invention may be in the form of a beverage, a soup, a dairy product, a snack and the like.

In one embodiment, the dietary supplement according to the present invention is a therapeutic dietary supplement. In another embodiment, the dietary supplement according to the present invention is a non-therapeutic dietary supplement.

In one embodiment, the food composition according to the present invention is a therapeutic food composition. In another embodiment, the food composition according to the present invention is a non-therapeutic food composition.

Another object of the present invention is a composition comprising the Brassicaceae protein extract or derivative thereof as described herein.

Another object of the present invention is a pharmaceutical composition comprising the Brassicaceae protein extract or derivative thereof as described herein, and at least one pharmaceutically acceptable excipient, and uses thereof.

In one embodiment, the pharmaceutical composition of the invention comprises a therapeutically effective amount of the Brassicaceae protein extract or derivative thereof according to the invention.

Another object of the present invention is a medicament comprising a Brassicaceae protein extract or derivative thereof as described herein.

In one embodiment, the medicament of the invention comprises a therapeutically effective amount of the Brassicaceae protein extract or derivative thereof according to the invention.

The present invention further relates to a method of inducing satiation in a subject in need thereof comprising administering to the subject an effective amount of a Brassicaceae protein extract or derivative thereof, composition, pharmaceutical composition, medicament, dietary supplement or food composition according to the invention.

One aspect of the present invention relates to a Brassicaceae protein extract or derivative thereof, composition, pharmaceutical composition, medicament, dietary supplement or food composition, for use for inducing satiation in a subject in need thereof.

One aspect of the present invention concerns the non-therapeutic use of Brassicaceae protein extract or derivative thereof, composition, dietary supplement or food composition, for inducing satiation in a subject. In one embodiment, the non-therapeutic use of a Brassicaceae protein extract or derivative thereof, composition, dietary supplement or food composition, for inducing satiation in a subject is a cosmetic use.

The present invention also relates to a method of prolonging satiety in a subject in need thereof comprising administering to the subject an effective amount of a Brassicaceae protein extract or derivative thereof, composition, pharmaceutical composition, medicament, dietary supplement or food composition according to the invention.

One aspect of the present invention relates to a Brassicaceae protein extract or derivative thereof, composition, pharmaceutical composition, medicament, dietary supplement or food composition, for use for prolonging satiety in a subject in need thereof, in particular in an obese subject.

One aspect of the present invention concerns the non-therapeutic use of a Brassicaceae protein extract or derivative thereof, composition, dietary supplement or food composition, for prolonging satiety in a subject, in particular in a subject having normal weight or uncomplicated overweight. In one embodiment, the non-therapeutic use of a Brassicaceae protein extract or derivative thereof, composition, dietary supplement or food composition, for prolonging satiety in a subject is a cosmetic use.

In one embodiment, the prolongation of satiety is of at least 1%, 2%, 3%, 4%, 5%, 6%, 7%, 8%, 9% or 10%. In a particular embodiment, the prolongation of satiety is of at least 1%, 2%, 3%, 4%, 5%, 6%, 7%, 8%, 9% or 10% of the time elapsed between meals, preferably of the time elapsed between meals prior to administration of the protein extract or derivative thereof, composition, pharmaceutical composition, medicament, dietary supplement or food composition according to the invention. In one embodiment, the prolongation of satiety is of at least 15%, 20% or 25%. In a particular embodiment, the prolongation of satiety is of at least 15%, 20% or 25% of the time elapsed between meals, preferably of the time elapsed between meals prior to administration of the protein extract or derivative thereof, composition, pharmaceutical composition, medicament, dietary supplement or food composition according to the invention.

The present invention further relates to a method of reducing meal size in a subject in need thereof comprising administering to the subject an effective amount of a Brassicaceae protein extract or derivative thereof, composition, pharmaceutical composition, medicament, dietary supplement or food composition according to the invention.

One aspect of the present invention relates to a Brassicaceae protein extract or derivative thereof, composition, pharmaceutical composition, medicament, dietary supplement or food composition, for use for reducing meal size in a subject in need thereof, in particular in an obese subject.

One aspect of the present invention concerns the non-therapeutic use of a Brassicaceae protein extract or derivative thereof, composition, dietary supplement or food composition, for reducing meal size in a subject, in particular in a subject having normal weight or uncomplicated overweight. In one embodiment, the non-therapeutic use of a Brassicaceae protein extract or derivative thereof, composition, dietary supplement or food composition, for reducing meal size in a subject is a cosmetic use.

In one embodiment, the reduction of meal size is of at least 1%, 2%, 3%, 4%, 5%, 6%, 7%, 8%, 9% or 10%. In a particular embodiment, the reduction of meal size is of at least 1%, 2%, 3%, 4%, 5%, 6%, 7%, 8%, 9% or 10% of the meal size prior to administration of the Brassicaceae protein extract or derivative thereof, composition, pharmaceutical composition, medicament, dietary supplement or food composition according to the invention. In one embodiment, the reduction of meal size is of at least 15%, 20% or 25%. In a particular embodiment, the reduction of meal size is of at least 15%, 20% or 25% of the meal size prior to administration of the Brassicaceae protein extract or derivative thereof, composition, pharmaceutical composition, medicament, dietary supplement or food composition according to the invention.

Another object of the present invention relates to a method of reducing food intake in a subject in need thereof comprising administering to the subject an effective amount of a Brassicaceae protein extract or derivative thereof, composition, pharmaceutical composition, medicament, dietary supplement or food composition according to the invention.

One aspect of the present invention relates to a Brassicaceae protein extract or derivative thereof, composition, pharmaceutical composition, medicament, dietary supplement or food composition, for use for reducing food intake in a subject in need thereof, in particular in an obese subject.

One aspect of the present invention concerns the non-therapeutic use of a Brassicaceae protein extract or derivative thereof, composition, dietary supplement or food composition, for reducing food intake in a subject, in particular in a subject having normal weight or uncomplicated overweight. In one embodiment, the non-therapeutic use of a Brassicaceae protein extract or derivative thereof, composition, dietary supplement or food composition, for reducing food intake in a subject is a cosmetic use.

In one embodiment, the reduction of food intake is of at least 1%, 2%, 3%, 4%, 5%, 6%, 7%, 8%, 9% or 10%. In a particular embodiment, the reduction of food intake is of at least 1%, 2%, 3%, 4%, 5%, 6%, 7%, 8%, 9% or 10% of the food intake prior to administration of the Brassicaceae protein extract or derivative thereof, composition, pharmaceutical composition, medicament, dietary supplement or food composition according to the invention. In one embodiment, the reduction of food intake is of at least 15%, 20% or 25%. In a particular embodiment, the reduction of food intake is of at least 15%, 20% or 25% of the food intake prior to administration of the Brassicaceae protein extract or derivative thereof, composition, pharmaceutical composition, medicament, dietary supplement or food composition according to the invention.

Another object of the present invention also relates to a method of controlling, in particular reducing, weight gain in a subject in need thereof comprising administering to the subject an effective amount of a Brassicaceae protein extract or derivative thereof, composition, pharmaceutical composition, medicament, dietary supplement or food composition according to the invention.

One aspect of the present invention relates to a Brassicaceae protein extract or derivative thereof, composition, pharmaceutical composition, medicament, dietary supplement or food composition, for use for controlling, in particular reducing, weight gain in a subject in need thereof, in particular in an obese subject.

One aspect of the present invention concerns the non-therapeutic use of a Brassicaceae protein extract or derivative thereof, composition, dietary supplement or food composition, for controlling, in particular reducing, weight gain in a subject, in particular in a subject having normal weight or uncomplicated overweight. In one embodiment, the non-therapeutic use of a Brassicaceae protein extract or derivative thereof, composition, dietary supplement or food composition, for controlling, in particular reducing, weight gain in a subject is a cosmetic use.

The present invention also relates to a method of stimulating weight loss in a subject in need thereof comprising administering to the subject an effective amount of a Brassicaceae protein extract or derivative thereof, composition, pharmaceutical composition, medicament, dietary supplement or food composition according to the invention.

One aspect of the present invention relates to a Brassicaceae protein extract or derivative thereof, composition, pharmaceutical composition, medicament, dietary supplement or food composition, for use for stimulating weight loss in a subject in need thereof, in particular in an obese subject.

One aspect of the present invention concerns the non-therapeutic use of a Brassicaceae protein extract or derivative thereof, composition, dietary supplement or food composition, for stimulating weight loss in a subject, in particular in a subject having normal weight or uncomplicated overweight. In one embodiment, the non-therapeutic use of a Brassicaceae protein extract or derivative thereof, composition, dietary supplement or food composition, for stimulating weight loss in a subject is a cosmetic use.

In one embodiment, the stimulation of weight loss is of at least 1%, 2%, 3%, 4%, 5%, 6%, 7%, 8%, 9% or 10%. In a particular embodiment, the stimulation of weight loss is of at least 1%, 2%, 3%, 4%, 5%, 6%, 7%, 8%, 9% or 10% of the weight loss of the subject prior to administration of the Brassicaceae protein extract or derivative thereof, composition, pharmaceutical composition, medicament, dietary supplement or food composition according to the invention. In one embodiment, the stimulation of weight loss is of at least 15%, 20% or 25%. In a particular embodiment, the stimulation of weight loss is of at least 15%, 20% or 25% of the weight loss of the subject prior to administration of the Brassicaceae protein extract or derivative thereof, composition, pharmaceutical composition, medicament, dietary supplement or food composition according to the invention.

The present invention further relates to a method of reducing weight in a subject in need thereof comprising administering to the subject an effective amount of a Brassicaceae protein extract or derivative thereof, composition, pharmaceutical composition, medicament, dietary supplement or food composition according to the invention.

One aspect of the present invention relates to a Brassicaceae protein extract or derivative thereof, composition, pharmaceutical composition, medicament, dietary supplement or food composition, for use for reducing weight in a subject in need thereof, in particular in an obese subject.

One aspect of the present invention concerns the non-therapeutic use of a Brassicaceae protein extract or derivative thereof, composition, dietary supplement or food composition, for reducing weight in a subject, in particular in a subject having normal weight or uncomplicated overweight. In one embodiment, the non-therapeutic use of a Brassicaceae protein extract or derivative thereof, composition, dietary supplement or food composition, for reducing weight in a subject is a cosmetic use.

In one embodiment, the reduction of weight is of at least 1%, 2%, 3%, 4%, 5%, 6%, 7%, 8%, 9% or 10%. In a particular embodiment, the reduction of weight is of at least 1%, 2%, 3%, 4%, 5%, 6%, 7%, 8%, 9% or 10% of the body weight of the subject prior to administration of the Brassicaceae protein extract or derivative thereof, composition, pharmaceutical composition, medicament, dietary supplement or food composition according to the invention. In one embodiment, the reduction of weight is of at least 15%, 20% or 25%. In a particular embodiment, the reduction of weight is of at least 15%, 20% or 25% of the body weight of the subject prior to administration of the Brassicaceae protein extract or derivative thereof, composition, pharmaceutical composition, medicament, dietary supplement or food composition according to the invention.

Another object of the present invention relates to a method of reducing fat mass on lean mass ratio in a subject in need thereof, comprising administering to the subject an effective amount of a Brassicaceae protein extract or derivative thereof, composition, pharmaceutical composition, medicament, dietary supplement or food composition according to the invention.

One aspect of the present invention relates to a Brassicaceae protein extract or derivative thereof, composition, pharmaceutical composition, medicament, dietary supplement or food composition, for use for reducing fat mass on lean mass ratio in a subject in need thereof, in particular in an obese subject.

One aspect of the present invention concerns the non-therapeutic use of a Brassicaceae protein extract or derivative thereof, composition, dietary supplement or food composition, for reducing fat mass on lean mass ratio in a subject, in particular in a subject having normal weight or uncomplicated overweight. In one embodiment, the non-therapeutic use of a Brassicaceae protein extract or derivative thereof, composition, dietary supplement or food composition, for reducing fat mass on lean mass ratio in a subject is a cosmetic use.

In one embodiment, the reduction of fat mass on lean mass ratio is of at least 1%, 2%, 3%, 4%, 5%, 6%, 7%, 8%, 9% or 10%. In a particular embodiment, the reduction of fat mass on lean mass ratio is of at least 1%, 2%, 3%, 4%, 5%, 6%, 7%, 8%, 9% or 10% of the fat mass on lean mass ratio of the subject prior to administration of the Brassicaceae protein extract or derivative thereof, composition, pharmaceutical composition, medicament, dietary supplement or food composition according to the invention. In one embodiment, the s reduction of fat mass on lean mass ratio is of at least 15%, 20% or 25%. In a particular embodiment, the reduction of fat mass on lean mass ratio is of at least 15%, 20% or 25% of the fat mass on lean mass ratio of the subject prior to administration of the Brassicaceae protein extract or derivative thereof, composition, pharmaceutical composition, medicament, dietary supplement or food composition according to the invention.

The present invention also relates to Brassicaceae protein extract or derivative thereof, a pharmaceutical composition or a medicament as described hereinabove, for use for treating inflammation in a subject in need thereof.

Within the meaning of the invention, by "inflammation", it is meant, as defined in Dorland's Medical Dictionary, "a localized protective response, elicited by injury or destruction of tissues, which serves to destroy, dilute or wall off both the injurious agent and the injured tissue". It is characterized by fenestration of the microvasculature, leakage of the elements of blood into the interstitial spaces, and migration of leukocytes into the inflamed tissue. On a macroscopic level, this is usually accompanied by the familiar clinical signs of erythema, edema, hyperalgesia (tenderness), and pain.

In one embodiment, the Brassicaceae protein extract or derivative thereof, a pharmaceutical composition or a medicament according to the invention is for use in the treatment of inflammation, wherein said inflammation is selected from the group comprising obesity, obesity-related diseases or disorders, neuroinflammation, multiple sclerosis, atherosclerosis, allergies, ankylosing spondylitis, arthritis (osteoarthritis, rheumatoid arthritis, or psoriatic arthritis), asthma, graft versus host disease, Parkinson's disease, Alzheimer's disease, Crohn's disease, colitis, dermatitis, diverticulitis, fibromyalgia, hepatitis, irritable bowel syndrome, systemic lupus erythematous, nephritis, and ulcerative colitis.

In one embodiment, the inflammation of the invention is an acute inflammation. In another embodiment, the inflammation of the invention is a chronic inflammation.

In one embodiment, the Brassicaceae protein extract or derivative thereof, a pharmaceutical composition or a medicament according to the invention is for use in the treatment of inflammation, wherein said inflammation is selected from the group comprising or consisting of obesity, obesity-related diseases or disorders, neuroinflammation, multiple sclerosis, psoriasis, allergic rhinitis, osteoarthritis and neuroinflammatory diseases. In a particular embodiment, the Brassicaceae protein extract or derivative thereof, a pharmaceutical composition or a medicament according to the invention is for use in the treatment of inflammation, wherein said inflammation is selected from the group comprising or consisting of obesity, neuroinflammation, multiple sclerosis, psoriasis, allergic rhinitis, osteoarthritis and neuroinflammatory diseases.

An object of the present invention relates to a Brassicaceae protein extract or derivative thereof, a pharmaceutical composition or a medicament according to the invention for use in the treatment or prevention of obesity in a subject in need thereof.

Another object of the present invention relates to a method for treating or preventing obesity in a subject in need thereof, comprising administering to the subject an effective amount of a Brassicaceae protein extract or derivative thereof, a pharmaceutical composition or a medicament as described hereinabove.

One aspect of the present invention relates to a Brassicaceae protein extract or derivative thereof, a pharmaceutical composition or a medicament according to the invention for use in the treatment or prevention of overweight and/or obesity-related diseases and disorders.

Another aspect of the present invention relates to a method for treating or preventing overweight and/or obesity-related diseases and disorders in a subject in need thereof, comprising administering to the subject an effective amount of a Brassicaceae protein extract or derivative thereof, a pharmaceutical composition or a medicament as described hereinabove.

In one embodiment, overweight and/or obesity-related diseases and disorders include, but are not limited to, high blood pressure, diabetes (in particular, type 2 diabetes), glucose intolerance, insulin resistance, cardiovascular disease (such as atherosclerosis, coronary artery disease, narrowed arteries, angina, heart attack, blood clots), high cholesterol, fatty liver disease, hepatic steatosis, cholelithiasis, joint problems, osteoarthritis, orthopedic problems, impaired balance, skin conditions, sleep apnea, respiratory problems, asthma, heavy snoring, cancer (including breast, colon, gallbladder, uterus, colon and prostate cancers), metabolic syndrome, menstrual abnormalities and psychosocial effects.

In some embodiments, the subject is a female. In some embodiments, the subject is a male.

In some embodiments, the subject is a child, such as an individual aged 3, 4, 5, 6, 7, 8, 9, 10, 11, 12, 13, 14, 15, 16, 17, or 18 (in human years). In some embodiments, the subject is an adult, such as an individual aged 18 or more (in human years).

In one embodiment, the subject is obese. Accordingly, in one embodiment, the subject has a body mass index (BMI) above 30. In one embodiment, the subject is moderately obese. Accordingly, in one embodiment, the subject has a BMI ranging from about 30 to about 35. In one embodiment, the subject is severely obese. Accordingly, in one embodiment, the subject has a BMI ranging from about 35 to about 40. In one embodiment, the subject is morbidly obese. Accordingly, in one embodiment, the subject has a BMI ranging from about 40 to about 50 or more.

In another embodiment, the subject is not obese. Accordingly, in one embodiment, the subject has a BMI below 30. In one embodiment, the subject is overweight. Accordingly, in one embodiment, the subject has a BMI ranging from about 25 to about 30. In one embodiment, the subject is a healthy overweight subject. In another embodiment, the subject is a non-healthy overweight subject. In one embodiment, the subject has a normal body weight. Accordingly, in one embodiment, the subject has a BMI ranging from about 18.5 and 25.

In one embodiment, the subject is under a slimming diet and/or wants to lose weight. In another embodiment, the subject is not under a slimming diet and/or does not want to lose weight.

In one embodiment, the subject is at risk of gaining weight. In one embodiment, the subject is at risk of accumulating excessive fat.

In one embodiment, the subject is at risk of developing overweight and/or obesity. In one embodiment, the subject is at risk of developing overweight and/or obesity-related diseases and disorders.

In one embodiment, the subject is a binge-eater. In one embodiment, the subject suffers from binge- or compulsive eating disorder.

In one embodiment, the Brassicaceae protein extract or derivative thereof is administered to the subject in the form of a composition, pharmaceutical composition, medicament, dietary supplement or food composition. In one embodiment, the Brassicaceae protein extract or derivative thereof is combined with pharmaceutically acceptable excipients, and optionally sustained-release matrices, such as biodegradable polymers, to form pharmaceutical compositions.

In one embodiment, the Brassicaceae protein extract or derivative thereof, composition, pharmaceutical composition, medicament, dietary supplement or food composition of the present invention is to be administered orally, topically, or by injection, preferably systemically injected.

Examples of formulations adapted to oral administration include, but are not limited to: solid forms, liquid forms and gels. Examples of solid forms adapted to oral administration include, but are not limited to, pill, tablet, capsule, soft gelatine capsule, hard gelatine capsule, caplet, compressed tablet, cachet, wafer, sugar-coated pill, sugar coated tablet, or dispersing/or disintegrating tablet, powder, solid forms suitable for solution in, or suspension in, liquid prior to oral administration and effervescent tablet. Examples of liquid form adapted to oral administration include, but are not limited to, solutions, suspensions, drinkable solutions, elixirs, sealed phial, potion, drench, syrup and liquor.

Examples of formulations adapted to topical administration include, but are not limited to, sticks, waxes, creams, lotions, ointments, balms, gels, masks, leave-on washes and/or the like.

In another embodiment, the Brassicaceae protein extract or derivative thereof, composition, pharmaceutical composition, or medicament of the present invention can also be applied topically using a transdermal system, such as one of an acrylic-based polymer adhesive with a resinous cross-linking agent impregnated with the composition and laminated to an impermeable backing. Examples of formulations adapted to transdermal administration include, but are not limited to, ointment, paste, cream, film, balm, patch, such as, for example, transdermal patch, gel, liposomal forms and the like.

Examples of formulations adapted to systemic injections include, but are not limited to: liquid solutions or suspensions, solid forms suitable for solution in, or suspension in, liquid prior to injection. Examples of systemic injections include, but are not limited to, intravenous, subcutaneous, intramuscular, intradermal, intravitreal, and intraperitoneal injection, or perfusion. In another embodiment, when injected, the composition, the pharmaceutical composition or the medicament of the invention is sterile. Methods for obtaining a sterile pharmaceutical composition include, but are not limited to, GMP synthesis (GMP stands for "Good manufacturing practice").

In one embodiment, the Brassicaceae protein extract or derivative thereof, composition, pharmaceutical composition, medicament, dietary supplement or food composition of the present invention is administered in a controlled-release, delayed-release, extended-release, long-acting-release, modified-release, sustained-release or timed-release form. Therefore, the Brassicaceae protein extract or derivative thereof, composition, pharmaceutical composition, dietary supplement or food composition of the invention further comprise sustained-release matrices, such as biodegradable polymers.

The disclosed extracts and derivatives thereof can be delivered to the target location in a variety of ways. The delivery mechanism chosen will depend in part on the target location, and whether the delivery is occurring for example in vivo or in vitro. Preferably, the target location is the intestine. More preferably, the target location is the intestinal enteroendocrine cells. The skilled artisan will be able to adapt the delivery of the extracts and derivatives thereof of the invention.

In one embodiment, the protein extract, composition, pharmaceutical composition, medicament, dietary supplement or food composition of the present invention is administered at least once a day, twice a day, or at least three times a day.

In another embodiment, the protein extract, composition, pharmaceutical composition, medicament, dietary supplement or food composition of the present invention is administered every day, every two, three, four, five, six or seven days.

In another embodiment, the protein extract, composition, pharmaceutical composition, medicament, dietary supplement or food composition of the present invention is administered every week, twice a week, every two weeks, or once a month.

In another embodiment, the protein extract, composition, pharmaceutical composition, medicament, dietary supplement or food composition of the present invention is administered every month for a period at least 2, 3, 4, 5 or 6 months.

In one embodiment, the method of the invention is for a chronic treatment, i.e., the protein extract, composition, pharmaceutical composition, medicament, dietary supplement or food composition of the present invention is administered for a prolonged period of time, such as, for example, for at least about 1 week, 1 month, 1 year or more.

In another embodiment, the method of the invention is for an acute treatment, such as, for example, a treatment with only 1, 2 or 3 administrations of the protein extract, composition, pharmaceutical composition, medicament, dietary supplement or food composition of the present invention.

In one embodiment, the administration of the protein extract, composition, pharmaceutical composition, medicament, dietary supplement or food composition of the present invention is repeated, for example, 2 to 3 times a day, for one day or more and generally for a sustained period of at least 4 days, or even 4 to 15 weeks, with, where appropriate, one or more periods of interruption.

In one embodiment, the protein extract, composition, pharmaceutical composition, medicament, dietary supplement or food composition of the present invention is administered simultaneously or sequentially with one meal of the subject. In one embodiment, the protein extract, composition, pharmaceutical composition, medicament, dietary supplement or food composition of the present invention is administered prior to the meal of the subject.

The present invention also relates to a kit comprising the Brassicaceae protein extract or derivative thereof, composition, pharmaceutical composition, medicament, dietary supplement or food composition according to the invention.

In one embodiment, the kit of the invention further comprises means to administer the Brassicaceae protein extract or derivative thereof, composition, pharmaceutical composition, medicament, dietary supplement or food composition according to the invention to a subject in need thereof.

Means to administer the Brassicaceae protein extract or derivative thereof, composition, pharmaceutical composition, dietary supplement or food composition according to the invention include, but are not limited to, syringes, needles, and other materials. In some embodiments, a means to administer the Brassicaceae protein extract or derivative thereof, composition, pharmaceutical composition, medicament, dietary supplement or food composition according to the invention include syringes pre-filled with the Brassicaceae protein extract or derivative thereof, composition, pharmaceutical composition, medicament, dietary supplement or food composition according to the invention of the invention.

In one embodiment, the kit of the invention further comprises instructions for the administration of the Brassicaceae protein extract or derivative thereof, composition, pharmaceutical composition, medicament, dietary supplement or food composition according to the invention to said subject.

In one embodiment, the kit of the invention is used for treating or preventing inflammation in a subject in need thereof, preferably for treating or preventing obesity, obesity-related diseases or disorders, and/or overweight-related diseases or disorders.

In one embodiment, the kit of the invention is used for preventing inducing satiation, prolonging satiety, reducing meal size, reducing food intake, controlling weight gain, reducing weight gain, stimulating weight loss, reducing weight and/or reducing fat mass on lean mass ratio in a subject.

The invention will be further illustrated by the following figures and examples. However, these examples and figures should not be interpreted in any way as limiting the scope of the present invention.

EXAMPLES

The present invention is further illustrated by the following examples.

Example 1: Analysis of Brassicaceae Proteins

The inventors have investigated the proteins present in some Brassicaceae. Among analyses, the inventors showed that a protein, the ClpB protein, present a substantial amino acid homology with the sequence of the α-MSH peptide (SEQ ID NO: 2).

In particular, the inventors showed that this protein comprises the following properties (FIG. 1):
1. presence of consecutive Arg and Trp which are two critical amino acids in the α-MSH pharmacophore (R543W544 in SEQ ID NO: 1) necessary for activation of MC receptors;
2. presence of the GIPV sequence homology (75%) with GKPV10-13 of α-MSH (GIPV546-549 in SEQ ID NO: 1);
3. presence of a negatively charged Glu homologous to Glu at position 5 in α-MSH (E539 in SEQ ID NO:1) which can be important for the protein/peptide folding and exposing the central RW sequence at the β-turn.

These results are presented with the amino acid sequence of the ClpB protein of *A. thaliana* (SEQ ID NO:1), but the same results were obtained with ClpB sequence of other Brassicaceae species (data not shown).

Example 2: Identification of Brassicaceae Proteins

To pursue the identification of the Brassicaceae proteins, western blot analyses were performed.

Material & Methods

Protein Extraction

Several species of Brassicaceae (white cabbage and green cabbage) were cut into small pieces and immediately frozen in liquid azote, then grinded.

Total proteins from the powder from the Brassicaceae sources were extracted by 30 second sonication in cytosolic protein extraction buffer (10 mM Hepes pH 7.9, 10 mM KCl, MgCl2 1.5 mM, EDTA 0.1 mM, DTT 1 mM, NP40 0.25%, PMSF 1 mM, phosphatase inhibitor P2850 1%, protease inhibitor P8340 0.5%). Then, the homogenate was centrifugated 2 min at 15000 rpm at 4° C.

The supernatant containing proteins was sampled and dosed by the BCA kit (Thermo Scientific, USA) to determine protein concentrations in each sample according to the manufacturer instructions. Briefly, 25 µL of each standard (working range=20-2000 µg/mL) or sample diluted at 1/200 were deposed in duplicate into a microplate well. Then, 200 µL BCA reagent mix (50 parts of BCA Reagent A with 1 part of BCA Reagent B) was added into each well and the plate was incubated 30 minutes at 37° C. in the dark. After incubation, optical density was measured at 562 nm. Sample concentrations were determined using the linear equation from the standard curve.

Western Blot Analysis

Protein samples (150 µg) were separated on 20% acrylamide SDS gel in Tris-Glycine buffer and transferred to a nitrocellulose membrane (GE Healthcare, Orsay, France), which was blocked for at least 1 h at room temperature with 5% (w/v) non-fat dry milk in TBS (10 mmol/L Tris, pH 8; 150 mmol/L NaCl) plus 0.05% (w/v) Tween 20. Then, the membrane was incubated overnight at 4° C. with rabbit polyclonal anti-α-MSH antibodies (1:500, Delphi Genetics), or rabbit polyclonal anti-*E. coli* ClpB antibodies (1:500, Delphi Genetics). After three washes in a blocking solution of 5% (w/v) non-fat dry milk in TBS/0.05% Tween 20, membranes were incubated for 1 h with peroxidase-conjugated anti-rabbit IgG (1:1000, SantaCruz Biotechnology). After three washes, the peroxidase reaction was revealed using the ECL detection kit (GE Healthcare). Protein bands were compared with the molecular weight standard (Precision Plus, BioRad) and films were scanned using ImageScanner III (GE Healthcare).

Results

Using either anti-ClpB or anti-α-MSH antibodies, full-size and fragments of ClpB were observed in the different sources of Brassicaceae (FIG. 2). Therefore, these results confirm the presence of ClpB and fragments thereof in protein extracts of Brassicaceae.

Example 3: Effects of Proteins of the Invention on PYY and GLP-1 Release

To determine the properties of proteins of the invention, their effects on release of PYY is assessed.

Material & Methods

Cell Culture

After euthanasia, rat colon is sampled and washed with fresh phosphate buffer saline (PBS). Intestinal tissue is then washed with L-15 medium (Leibovitz-15 medium; Sigma-Aldrich, Mo, US) maintaining a physiologic pH. Colic mucosa is scraped and digested with 0.4 mg/mL of collagenase IX (Psichas et al., 2015. Int J Obes (Lond). 39(3): 424-9) in high glucose DMEM (Dulbecco's Modified Eagle Medium; Dominique Dutscher, France—supplemented with 5.5 mmol/L of L-glutamine, 100 U/mL of penicillin, 0.1 mg/mL of streptomycin and non-essential amino acids) at 37° C. during 5-10 minutes. Cell suspensions are centrifuged at 750 rpm during 8 minutes and intestinal cells are suspended in the same supplemented DMEM medium in which 10% of fetal bovine serum is added. Cell suspensions are filtered at 100 µm (Merck Millipore, Mass, USA) and cultured into 24 wells plate coated with 1% Matrigel (Corning, N.Y., US). Finally, plates are incubated overnight at 37° C. in a 95% O2/5% CO2 atmosphere.

Cell Lysate Preparation

The solution containing Brassicaceae proteins as disclosed in the previous Example is sampled and dosed to determine total protein concentration.

Concomitantly, intestinal cells are incubated in secretion buffer pH 7.4 (4.5 mM of KCl, 138 mM of NaCl, 4.2 mM of NaHCO3, 1.2 mM de NaH2PO4, 2.6 mM de CaCl2, 1.2 mM de MgCl2 and 10 mM of HEPES). Then, cells are incubated during 20 minutes at 37° C. in the solution containing Brassicaceae proteins. As a control, cells are also incubated in PBS.

After incubation, supernatants are sampled, centrifuged (10000 rpm during 3 minutes) and immediately stored at −80° C. Then, cells are treated with a lysis buffer (50 mmol/L Tris-HCl, 150 mmol/L NaCl, 1% IGEPAL-CA 630, 0.5% desoxycholic acid and protease inhibitor cocktail without EDTA) to extract intracellular peptides. Cell lysates are immediately frozen at −80° C. towards PYY measurements.

PYY Dosage

PYY dosage is performed on cell medium and cell lysates to measure PYY liberation (in the medium), production (within the lysates) and the total PYY relative production (medium and lysates). This dosage is realized using Fluorescent Immunoassay Kit® (Phoenix Pharmaceuticals, Inc.) according to the manufacturer instructions.

Briefly, after all reagent reconstitution, 50 µl of 1× assay buffer into 2 wells as total binding, 50 µl of prepared peptide standards, 50 µl of rehydrated positive control and 50 µl of prepared samples are charged onto the immunoplate. Then, 25 µl of rehydrated primary antibody and 25 µl of rehydrated biotinylated peptide are added into each well except the blank well. The microplate is incubated for 2 hours at room temperature (20-23° C.) under orbital shaking at 300-400 rpm. After incubation, each well is washed four times with 350 µl of 1× assay buffer and 100 µl of SA-HRP antibody solution previously prepared by diluting 12 µl of SA-HRP into 12 ml of 1× assay buffer was added. The immunoplate is incubated again for 1 hour at room temperature (20-23° C.) under orbital shaking at 300-400 rpm. After incubation, each well is washed in the same way as before and 100 µl of TMB substrate solution are added. The plate is incubated and protected from the light for 1 hour at room temperature (20-23° C.) under orbital shaking at 300-400 rpm.

At the end, 100 µl 2N HCl are added into each well to stop the reaction (the colour in the well changed from blue to yellow) and the immunoplate is read onto a microtiter plate reader. Absorbance in optical density is read at 450 nm.

The invention claimed is:

1. A method for stimulating weight loss, for reducing weight gain or for inducing satiation in a subject in need thereof, said method comprising administering to the subject an effective amount of a Brassicaceae protein extract comprising Brassicaceae ClpB presenting the amino acid sequence SEQ ID NO:1.

2. The method according to claim 1, wherein said Brassicaceae is a *Brassica* species.

3. The method according to claim 2, wherein said *Brassica* species is selected from the group comprising *Brassica oleracea, Brassica rapa, Brassica napus, Brassica nigra, Brassica carinata, Brassica juncea, Raphanus sativus, Armoracia rusticana, Matthiola* and *Arabidopsis thaliana*.

4. The method according to claim 1, wherein said Brassicaceae protein extract or derivative thereof comprises at least 10% by weight of proteins.

5. The method according to claim 1, wherein said Brassicaceae protein extract or derivative thereof comprises at least 20% by weight of proteins.

6. The method according to claim 1, wherein said Brassicaceae protein extract or derivative thereof comprises at least 30% by weight of proteins.

7. The method according to claim 1, wherein said Brassicaceae protein extract or derivative thereof comprises proteins and fibers, wherein the ratio proteins/fibers in weight is of at least 2.5.

8. The method according to claim 1, wherein the subject is not obese.

9. The method according to claim 1, wherein the subject is obese.

10. The method according to claim 1, wherein the subject is overweight.

11. The method according to claim 1, wherein said Brassicaceae protein extract or derivative thereof is administered to the subject in the form of a dietary supplement or food composition.

12. The method according to claim 11, wherein said dietary supplement or food composition further comprises at least one additional ingredient selected from the group comprising simple and/or complex carbohydrates, lipids, fibers, minerals or mixture thereof.

13. The method according to claim 1, wherein said Brassicaceae protein extract or derivative thereof is administered to the subject orally.

14. The method according to claim 1, wherein said Brassicaceae protein extract or derivative thereof is administered simultaneously or sequentially with one meal of the subject.

15. The method according to claim 1, wherein said Brassicaceae protein extract or derivative thereof is in the form of a kit comprising the Brassicaceae protein extract or derivative thereof and optionally means to administer said Brassicaceae protein extract or derivative thereof to the subject in need thereof.

16. The method according to claim 1, wherein said Brassicaceae is a *Brassica oleracea*.

17. The method according to claim 1, wherein said Brassicaceae protein extract or derivative thereof comprises proteins and fibers, wherein the ratio proteins/fibers in weight is of at least 3.

\* \* \* \* \*

SEQUENCE LISTING

<160> NUMBER OF SEQ ID NOS: 2

<210> SEQ ID NO 1
<211> LENGTH: 911
<212> TYPE: PRT
<213> ORGANISM: Arabidopsis thaliana
<220> FEATURE:
<223> OTHER INFORMATION: ClpB

<400> SEQUENCE: 1

```
Met Asn Pro Glu Lys Phe Thr His Lys Thr Asn Glu Thr Ile Ala Thr
1               5                   10                  15

Ala His Glu Leu Ala Val Asn Ala Gly His Ala Gln Phe Thr Pro Leu
            20                  25                  30

His Leu Ala Gly Ala Leu Ile Ser Asp Pro Thr Gly Ile Phe Pro Gln
        35                  40                  45

Ala Ile Ser Ser Ala Gly Gly Glu Asn Ala Ala Gln Ser Ala Glu Arg
    50                  55                  60

Val Ile Asn Gln Ala Leu Lys Lys Leu Pro Ser Gln Ser Pro Pro Pro
65                  70                  75                  80

Asp Asp Ile Pro Ala Ser Ser Ser Leu Ile Lys Val Ile Arg Arg Ala
```

```
                        85                  90                  95
            Gln Ala Ala Gln Lys Ser Arg Gly Asp Thr His Leu Ala Val Asp Gln
                        100                 105                 110

Leu Ile Met Gly Leu Leu Glu Asp Ser Gln Ile Arg Asp Leu Leu Asn
                        115                 120                 125

Glu Val Gly Val Ala Thr Ala Arg Val Lys Ser Glu Val Glu Lys Leu
                        130                 135                 140

Arg Gly Lys Glu Gly Lys Lys Val Glu Ala Ser Gly Asp Thr Asn
            145                 150                 155                 160

Phe Gln Ala Leu Lys Thr Tyr Gly Arg Asp Leu Val Glu Gln Ala Gly
                        165                 170                 175

Lys Leu Asp Pro Val Ile Gly Arg Asp Glu Glu Ile Arg Arg Val Val
                        180                 185                 190

Arg Ile Leu Ser Arg Arg Thr Lys Asn Asn Pro Val Leu Ile Gly Glu
                        195                 200                 205

Pro Gly Val Gly Lys Thr Ala Val Val Glu Gly Leu Ala Gln Arg Ile
                        210                 215                 220

Val Lys Gly Asp Val Pro Asn Ser Leu Thr Asp Val Arg Leu Ile Ser
            225                 230                 235                 240

Leu Asp Met Gly Ala Leu Val Ala Gly Ala Lys Tyr Arg Gly Glu Phe
                        245                 250                 255

Glu Glu Arg Leu Lys Ser Val Leu Lys Glu Val Glu Asp Ala Glu Gly
                        260                 265                 270

Lys Val Ile Leu Phe Ile Asp Glu Ile His Leu Val Leu Gly Ala Gly
                        275                 280                 285

Lys Thr Glu Gly Ser Met Asp Ala Ala Asn Leu Phe Lys Pro Met Leu
                        290                 295                 300

Ala Arg Gly Gln Leu Arg Cys Ile Gly Ala Thr Thr Leu Glu Glu Tyr
            305                 310                 315                 320

Arg Lys Tyr Val Glu Lys Asp Ala Ala Phe Glu Arg Arg Phe Gln Gln
                        325                 330                 335

Val Tyr Val Ala Glu Pro Ser Val Pro Asp Thr Ile Ser Ile Leu Arg
                        340                 345                 350

Gly Leu Lys Glu Lys Tyr Glu Gly His His Gly Val Arg Ile Gln Asp
                        355                 360                 365

Arg Ala Leu Ile Asn Ala Ala Gln Leu Ser Ala Arg Tyr Ile Thr Gly
                        370                 375                 380

Arg His Leu Pro Asp Lys Ala Ile Asp Leu Val Asp Glu Ala Cys Ala
            385                 390                 395                 400

Asn Val Arg Val Gln Leu Asp Ser Gln Pro Glu Glu Ile Asp Asn Leu
                        405                 410                 415

Glu Arg Lys Arg Met Gln Leu Glu Ile Glu Leu His Ala Leu Glu Arg
                        420                 425                 430

Glu Lys Asp Lys Ala Ser Lys Ala Arg Leu Ile Glu Val Arg Lys Glu
                        435                 440                 445

Leu Asp Asp Leu Arg Asp Lys Leu Gln Pro Leu Thr Met Lys Tyr Arg
                        450                 455                 460

Lys Glu Lys Glu Arg Ile Asp Glu Ile Arg Arg Leu Lys Gln Lys Arg
            465                 470                 475                 480

Glu Glu Leu Met Phe Ser Leu Gln Glu Ala Glu Arg Arg Tyr Asp Leu
                        485                 490                 495

Ala Arg Ala Ala Asp Leu Arg Tyr Gly Ala Ile Gln Glu Val Glu Ser
                        500                 505                 510
```

```
Ala Ile Ala Gln Leu Glu Gly Thr Ser Ser Glu Asn Val Met Leu
            515                 520                 525

Thr Glu Asn Val Gly Pro Glu His Ile Ala Glu Val Val Ser Arg Trp
        530                 535                 540

Thr Gly Ile Pro Val Thr Arg Leu Gly Gln Asn Glu Lys Glu Arg Leu
545                 550                 555                 560

Ile Gly Leu Ala Asp Arg Leu His Lys Arg Val Val Gly Gln Asn Gln
                565                 570                 575

Ala Val Asn Ala Val Ser Glu Ala Ile Leu Arg Ser Arg Ala Gly Leu
            580                 585                 590

Gly Arg Pro Gln Gln Pro Thr Gly Ser Phe Leu Phe Leu Gly Pro Thr
        595                 600                 605

Gly Val Gly Lys Thr Glu Leu Ala Lys Ala Leu Ala Glu Gln Leu Phe
        610                 615                 620

Asp Asp Glu Asn Leu Leu Val Arg Ile Asp Met Ser Glu Tyr Met Glu
625                 630                 635                 640

Gln His Ser Val Ser Arg Leu Ile Gly Ala Pro Pro Gly Tyr Val Gly
                645                 650                 655

His Glu Glu Gly Gly Gln Leu Thr Glu Ala Val Arg Arg Pro Tyr
            660                 665                 670

Cys Val Ile Leu Phe Asp Glu Val Lys Ala His Val Ala Val Phe
        675                 680                 685

Asn Thr Leu Leu Gln Val Leu Asp Asp Gly Arg Leu Thr Asp Gly Gln
        690                 695                 700

Gly Arg Thr Val Asp Phe Arg Asn Ser Val Ile Ile Met Thr Ser Asn
705                 710                 715                 720

Leu Gly Ala Glu His Leu Leu Ala Gly Leu Thr Gly Lys Val Thr Met
                725                 730                 735

Glu Val Ala Arg Asp Cys Val Met Arg Glu Val Arg Lys His Phe Arg
            740                 745                 750

Pro Glu Leu Leu Asn Arg Leu Asp Glu Ile Val Val Phe Asp Pro Leu
        755                 760                 765

Ser His Asp Gln Leu Arg Lys Val Ala Arg Leu Gln Met Lys Asp Val
        770                 775                 780

Ala Val Arg Leu Ala Glu Arg Gly Val Ala Leu Ala Val Thr Asp Ala
785                 790                 795                 800

Ala Leu Asp Tyr Ile Leu Ala Glu Ser Tyr Asp Pro Val Tyr Gly Ala
                805                 810                 815

Arg Pro Ile Arg Arg Trp Met Glu Lys Val Val Thr Glu Leu Ser
        820                 825                 830

Lys Met Val Val Arg Glu Glu Ile Asp Glu Asn Ser Thr Val Tyr Ile
                835                 840                 845

Asp Ala Gly Ala Gly Asp Leu Val Tyr Arg Val Glu Ser Gly Gly Leu
850                 855                 860

Val Asp Ala Ser Thr Gly Lys Lys Ser Asp Val Leu Ile His Ile Ala
865                 870                 875                 880

Asn Gly Pro Lys Arg Ser Asp Ala Ala Gln Ala Val Lys Lys Met Arg
                885                 890                 895

Ile Glu Glu Ile Glu Asp Asp Asn Glu Glu Met Ile Glu Asp
            900                 905                 910

<210> SEQ ID NO 2
<211> LENGTH: 13
```

```
<212> TYPE: PRT
<213> ORGANISM: Homo sapiens
<220> FEATURE:
<223> OTHER INFORMATION: N1-MSH

<400> SEQUENCE: 2

Ser Tyr Ser Met Glu His Phe Arg Trp Gly Lys Pro Val
1               5                   10
```